(12) United States Patent  
Maass et al.

(10) Patent No.: US 8,968,294 B2
(45) Date of Patent: Mar. 3, 2015

(54) SINGLE OR LIMITED USE DEVICE DESIGNS

(75) Inventors: Janet E. Maass, Loveland, CO (US); Jeffrey R. Townsend, Loveland, CO (US); Duane E. Kerr, Loveland, CO (US)

(73) Assignee: Covidien LP, Mansfield, MA (US)

( * ) Notice: Subject to any disclaimer, the term of this patent is extended or adjusted under 35 U.S.C. 154(b) by 529 days.

(21) Appl. No.: 13/448,794

(22) Filed: Apr. 17, 2012

(65) Prior Publication Data

US 2013/0274734 A1 Oct. 17, 2013

(51) Int. Cl.
*A61B 18/04* (2006.01)

(52) U.S. Cl.
USPC .......................................................... 606/34

(58) Field of Classification Search
CPC ........ A61B 18/00; A61B 18/02; A61B 18/04; A61N 1/00
USPC .......................................................... 606/34
See application file for complete search history.

(56) References Cited

U.S. PATENT DOCUMENTS

| | | | |
|---|---|---|---|
| 1,996,258 | A | 4/1935 | Ruskin |
| 6,522,234 | B1 | 2/2003 | Sturgill |
| 6,958,463 | B1 | 10/2005 | Kochman et al. |
| 7,041,096 | B2 | 5/2006 | Malis et al. |
| 2005/0239349 | A9 | 10/2005 | Desinger |
| 2010/0136856 | A1 | 6/2010 | Gleason et al. |

FOREIGN PATENT DOCUMENTS

| | | |
|---|---|---|
| EP | 2329783 A1 | 6/2011 |
| WO | WO 93/00862 A2 | 1/1993 |
| WO | WO 2005/060365 A2 | 7/2005 |
| WO | WO 2005/081730 A2 | 9/2005 |
| WO | WO 2007/136694 A2 | 11/2007 |

OTHER PUBLICATIONS

European Search Report dated Aug. 9, 2013 from corresponding EP Application No. 13163708.4. (5 pgs.).

*Primary Examiner* — Christopher D Koharski
*Assistant Examiner* — Elizabeth K So

(57) ABSTRACT

The present disclosure is directed to an electrosurgical system. The electrosurgical system includes an electrosurgical generator configured to output electrosurgical energy and including a receptacle having at least one mechanical interface. The system also includes an electrosurgical instrument adapted to connect to the electrosurgical generator and configured to deliver energy to tissue. Further, a plug is provided to engage the receptacle to electrically couple the electrosurgical instrument to the electrosurgical generator. The plug includes a terminal electrically coupled to the electrosurgical instrument and a prong electrically coupled to the terminal that includes a recess defined therein and is configured to receive the at least one mechanical interface. When the plug is disengaged from the receptacle, the at least one mechanical interface cooperates with the recess to uncouple the prong from the terminal.

11 Claims, 5 Drawing Sheets

SINGLE OR LIMITED USE DEVICE DESIGNS

BACKGROUND

1. Technical Field

The present disclosure relates to electrosurgical instruments used for open and endoscopic surgical procedures for sealing or fusing tissue. More particularly, the present disclosure relates to systems and methods for limiting the number of times an electrosurgical instrument can be used.

2. Background of the Related Art

Energy-based tissue treatment is well known in the art. Various types of energy (e.g., electrical, ultrasonic, microwave, cryogenic, thermal, laser, etc.) are applied to tissue to achieve a desired result. Electrosurgical instruments have become widely used by surgeons in recent years. By and large, most electrosurgical instruments are hand-held instruments, e.g., electrosurgical pencils, electrosurgical forceps, endoscopic instruments such as monopolar forceps, bipolar forceps or a combination monopolar/bipolar forceps, ultrasonic hand tools, microwave probes. Such electrosurgical instruments are electrically coupled to an external electrosurgical generator. Alternatively, the electrosurgical instruments may be portable and include a battery powered electrosurgical generator.

Electrosurgical instruments have a limited number of uses before they need to be discarded. Reusing the electrosurgical instrument after it has reached its limited number of uses may lead to complications during electrosurgery.

SUMMARY

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

As shown in the drawings and described throughout the following description, as is traditional when referring to relative positioning on a surgical instrument, the term "proximal" refers to the end of the apparatus that is closer to the user or generator and the term "distal" refers to the end of the apparatus that is farther away from the user or generator. The term "clinician" refers to any medical professional (i.e., doctor, surgeon, nurse, or the like) performing a medical procedure involving the use of aspects of the present disclosure described herein.

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second).

The phrase "electrosurgical instrument" may refer to any instrument configured to output electrosurgical energy such as electrosurgical pencils, electrosurgical forceps, endoscopic instruments such as monopolar forceps, bipolar forceps or a combination monopolar/bipolar forceps, ultrasonic hand tools, microwave probes.

In an aspect of the present disclosure, an electrosurgical system is provided that includes an electrosurgical generator configured to output electrosurgical energy. The electrosurgical generator includes a receptacle having at least one mechanical interface. The system also includes an electrosurgical instrument adapted to connect to the electrosurgical generator and configured to deliver energy to tissue and a plug configured to engage the receptacle to electrically couple the electrosurgical instrument to the electrosurgical generator. The plug includes a terminal electrically coupled to the electrosurgical instrument and a prong electrically coupled to the terminal, the prong includes a recess that is configured to receive the at least one mechanical interface. When the plug is disengaged from the receptacle, the at least one mechanical interface cooperates with the recess to uncouple the prong from the terminal.

The prong includes a pair of contacts that are electrically coupled to the terminal are biased in a spaced apart configuration. The plug may also include at least one tab, wherein upon disengagement of the plug from the receptacle the pair of contacts move proximally relative to the at least one tab thereby breaking the electrical coupling between the terminal and the prong.

In another aspect of the electrosurgical system, the plug may include a chamber defined therein filled with a conductive medium that provides electrical continuity between the terminal and the prong and wherein and a distal end of the prong seals the chamber. The conductive medium is released from the chamber thereby eliminating electrical continuity between the terminal and the prong and preventing further use of the electrosurgical instrument.

In yet another aspect of the present disclosure, an electrosurgical system is provided that includes an electrosurgical generator configured to output electrosurgical energy. The electrosurgical generator includes a receptacle having at least one mechanical interface. The system also includes an electrosurgical instrument adapted to connect to the electrosurgical generator and configured to deliver energy to tissue and a plug configured to engage the receptacle to electrically couple the electrosurgical instrument to the electrosurgical generator. The plug includes a conduit electrically coupled to the electrosurgical instrument, a prong configured to be electrically coupled to the receptacle, and a fuse electrically coupling the conduit to the prong. When the plug is disengaged from the receptacle, the at least one mechanical interface breaks the fuse to uncouple the prong from the conduit.

The fuse may be a wire and the mechanical interface may be a fuse cutter configured to cut the fuse. Alternatively, the mechanical interface may be a ram configured to stress and/or flex the fuse to break the fuse. The fuse is configured to break after the ram stresses and/or flexes the fuse a predetermined number of times.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1A:
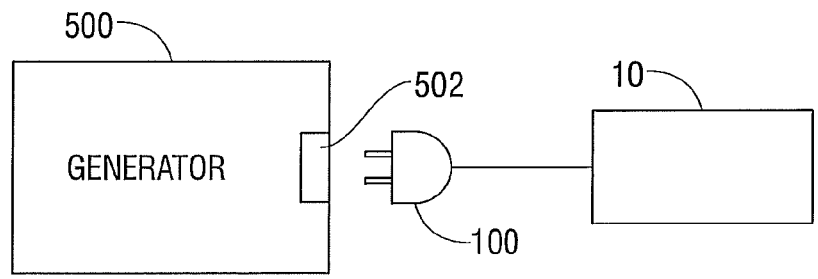
FIGS. 1A and 1B are system block diagrams of electrosurgical instruments.

Particular embodiments of the present disclosure are described hereinbelow with reference to the accompanying drawings; however, the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

Figure 1B:
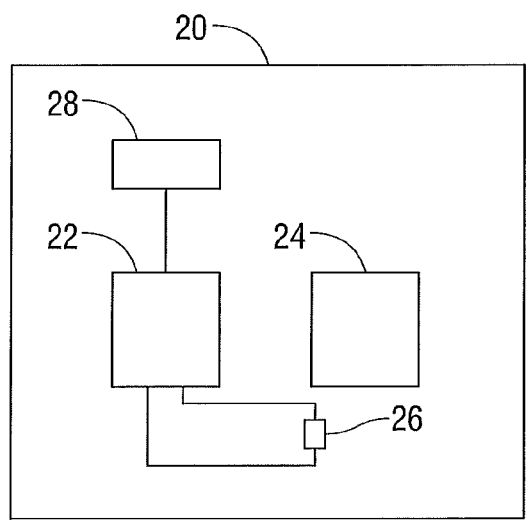
Figure 2A:
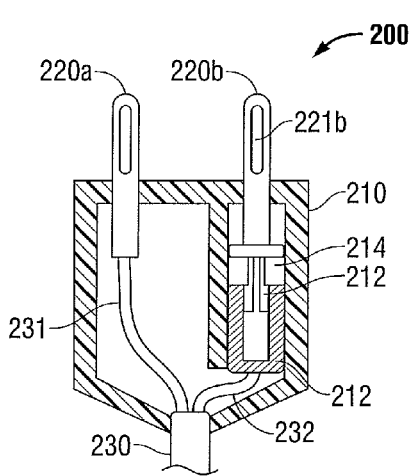
FIGS. 2A-2D are schematic diagrams of an electrosurgical plug and receptacle according to an embodiment of the present disclosure.
Figure 2B:
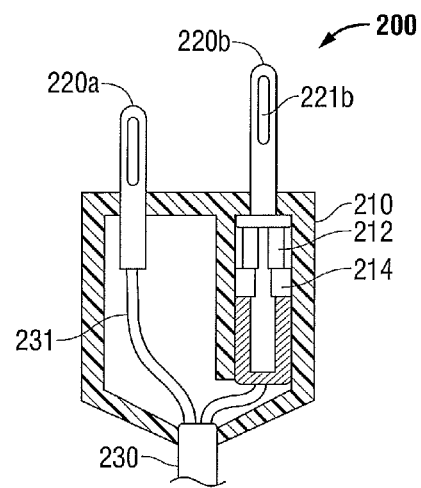
Figure 2C:
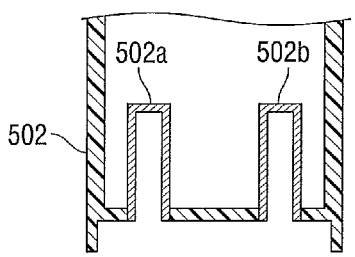
Figure 2D:
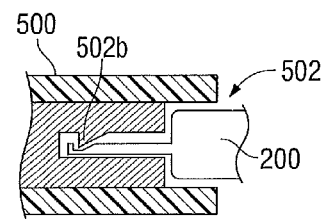

Turning to the figures, FIGS. 1A and 1B depict system block diagrams of electrosurgical instruments 10, 20 that have a single or limited use capability. As shown in FIG. 1A, electrosurgical instrument 10 includes an electrosurgical interface or plug 100 that connects electrosurgical instrument 10 to an electrosurgical generator 500. Plug 100 is inserted into a receptacle 502 of electrosurgical generator 500.

FIG. 1B depicts a system block diagram of an electrosurgical instrument 20 which may be a portable system or provided as separate components. Electrosurgical instrument 20 includes an electrosurgical generator 22, which includes a power source, a control unit, sensors, memory, which cooperate to generate an electrosurgical output to assembly 24 and measure responses therefrom. Assembly 24 may include a single electrode, multiple electrodes, one or more transducers, one or more antenna probes or a combination thereof. Generator 22 is electrically coupled to a fuse 26 and an activation button 28. Activation button 28 may be a push button switch, a toggle switch, lever, or any other mechanical device that may be used to activate electrosurgical instrument 20.

Turning to FIGS. 2A through 2D, a plug 200 according to an embodiment of the present disclosure is depicted. Plug 200 is electrically coupled to an electrosurgical instrument (not shown) via cable 230. Cable 230 includes at least two conduits 231 and 232. Conduits 231 and 232, which may be a wire or any other transmission medium that conducts electricity, are electrically coupled, either directly or indirectly, to prongs 220a and 220b, respectively. Conduit 232 is coupled to terminal 212 which is configured to receive the distal end of prong 220b. Distal end of prong 220b includes a pair of contacts 222 that are normally biased to be spaced apart and electrically coupled to terminal 212. Contacts 222 may be biased apart by a spring or any other resilient means suitable for keeping contacts 222 spaced relative to one another.

During operation of an electrosurgical instrument that includes plug 200, plug 200 engages receptacle 502 of an electrosurgical generator (see FIG. 1A). Prong 220b includes a recess 221b defined therein that is configured to engage a corresponding protrusion 502b in receptacle 502. Protrusion 502b can be any mechanical interface configured to mechanically engage recess 221b. After plug 200 engages receptacle 502 and upon activation of button 28, energy is supplied to electrosurgical instrument 10. In particular, conduit 232, terminal 212, contacts 222, prong 220b are electrically coupled to terminal 502b in receptacle 502 while conduit 231 and prong 220a are electrically coupled to terminal 502a thereby providing a path for energy. After the clinician finishes using the electrosurgical instrument 10, plug 200 is removed from receptacle 502. When plug 200 is removed, protrusion 502b cooperates with recess 221b to pull prong 220b proximally. Pulling prong 220b causes contacts 222 to be pulled proximally. After contacts 222 pass tabs 214, contacts 222 are fully spaced apart and rest on tabs 214 thereby preventing any further electrical coupling between contacts 222 and terminal 212.

Figure 3A:
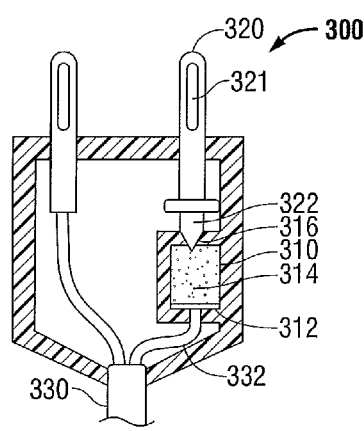
FIGS. 3A and 3B are schematic diagrams of an electrosurgical plug according to another embodiment of the present disclosure.
Figure 3B:
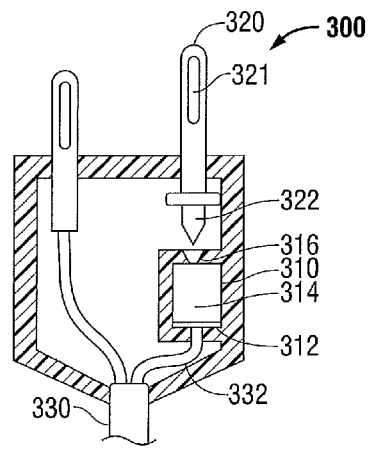

FIGS. 3A and 3B depict a plug 300 according to another embodiment of the present disclosure. Plug 300 includes a conduit 330 that is electrically coupled to an electrosurgical instrument 10. Conduit 330 includes a conduit 332 that is electrically coupled to terminal 312 in chamber 310. Chamber 310 is filled with a conductive gas 314 such as argon, carbon dioxide, helium, neon, hydrogen peroxide, etc. Gas 314 electrically couples terminal 312 to distal end 322 of prong 320. Distal end 322 seals aperture 316 defined in chamber 310 preventing gas 314 from escaping therefrom. Recess 321 of prong 320 engages protrusion 502b in receptacle 502 to pull prong 320 proximally when plug 300 is disengaged from receptacle 502. Disengaging plug 300 causes distal end 322 to disengage aperture 316 allowing gas 314 to escape from chamber 310 as shown in FIG. 3B. Without the conductive gas 314 being disposed in chamber 310, electrosurgical energy is prevented from being transmitted therethrough. Thus, plug 300 is prevented from being used in a subsequent procedure.

Figure 4A:
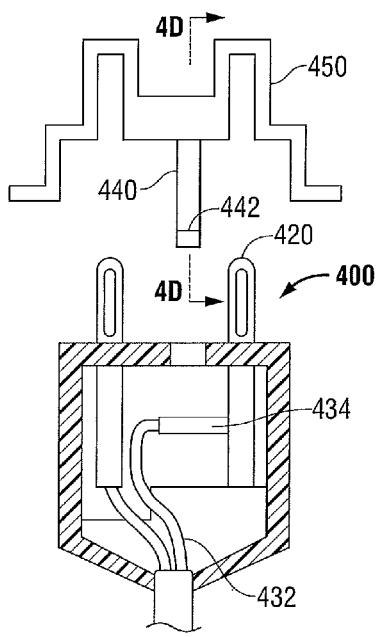
FIGS. 4A-4D are a schematic diagrams of an electrosurgical plug and receptacle according to another embodiment of the present disclosure.
Figure 4B:
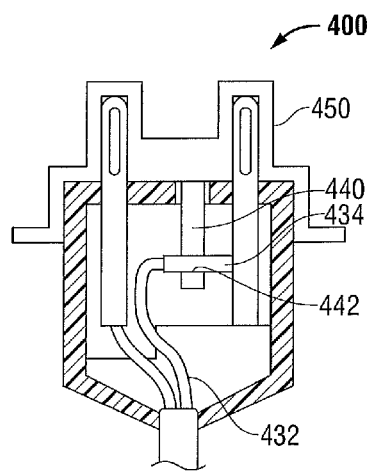
Figure 4C:
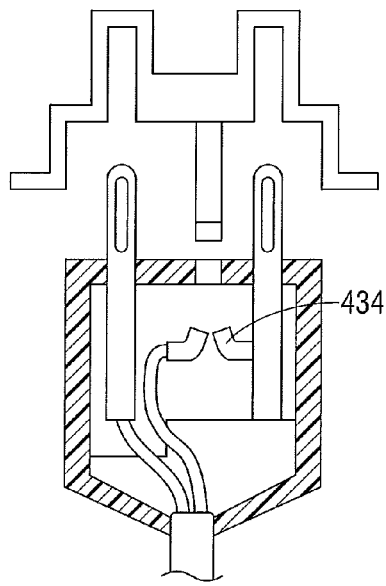
Figure 4D:
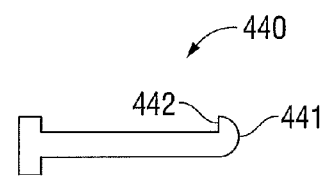

FIGS. 4A to 4D depict a plug 400 and receptacle 450 according to another embodiment of the present disclosure. Plug 400 includes a prong 420 that is electrically coupled to an electrosurgical instrument via a conduit 432 and a fuse 434. Fuse 434 may be a wire or any other conductive material. Receptacle 450 includes a mechanical interface or fuse cutter 440 having a sharp edge 442 (as shown in FIG. 4D). When plug 400 is inserted into receptacle 450, fuse 434 slides over the distal end 441 of fuse cutter 440. After plug 400 is removed, sharp edge 442 cuts fuse 434 severing the electrical connection between prong 420 and conduit 432 as shown in FIG. 4C thereby preventing electrosurgical instrument 10 from further use.

Figure 5:
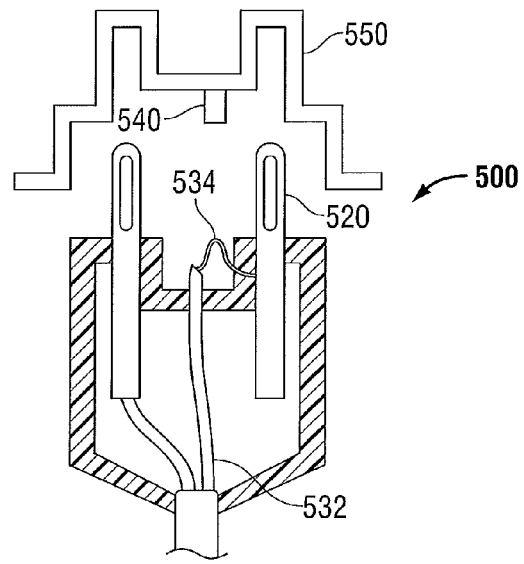
FIG. 5 is a schematic diagram of an electrosurgical plug according to another embodiment of the present disclosure.

FIG. 5 depicts a plug 500 and receptacle 550 according to another embodiment of the present disclosure. As shown in FIG. 5, plug 500 includes a prong 520 that is electrically coupled to conduit 532 via fuse 534. Receptacle 550 includes a flange or ram 540 having a flat surface on a distal end thereof. When plug 500 is inserted into receptacle 550, ram 540 makes contact with fuse 534 and causes fuse 534 to be flexed and/or stressed. Fuse 534 is designed to break after ram 540 engages fuse 534 one or a predetermined number of times.

Figure 6:
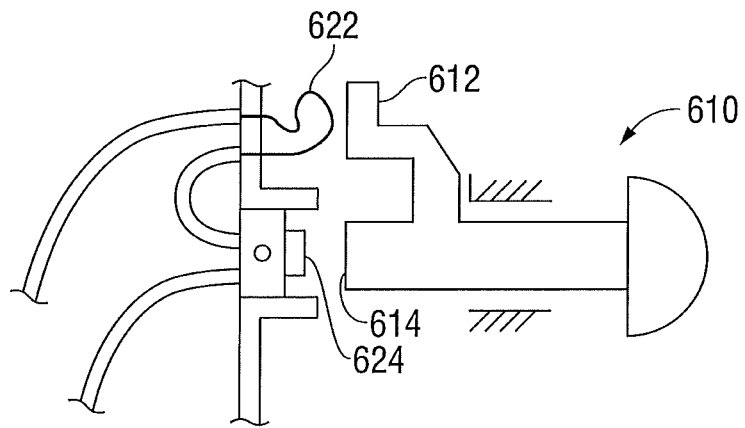
FIG. 6 is a schematic diagram of an activation switch assembly according to another embodiment of the present disclosure.
Figure 7:
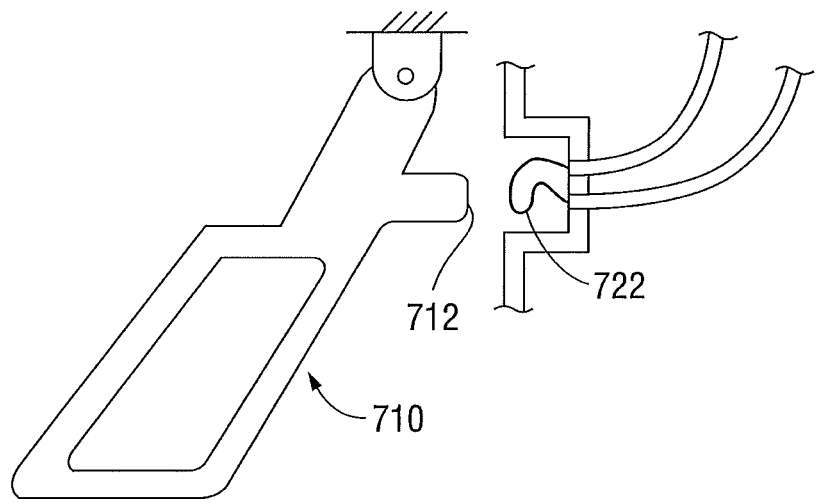
FIG. 7 is a schematic diagram of a lever assembly according to another embodiment of the present disclosure.

FIGS. 6 and 7 depict different embodiments for use with electrosurgical instrument 20 of FIG. 1B. The embodiments shown in FIGS. 6 and 7 can be used to limit use of electrosurgical instrument 20 for a predetermined number of times. For instance as shown in FIG. 6, electrosurgical instrument 20 may include an activation button 610 having ram 612 and a surface 614. When activation button 610 is pressed, surface 614 engages a push button switch 624 thus activating electrosurgical instrument 20. Surface 614 may be a conductive surface and push button switch 624 may be replaced by a pair of non-contacting electrodes (not shown) such that when activation button 610 is depressed, second surface 614 contacts the pair of electrodes to activate the electrosurgical instrument. While activation button 610 is depressed, ram 612 causes fuse 622 to flex and/or stress. Fuse 622 may be designed to break after ram 612 engages fuse 622 a predetermined number of times.

As shown in FIG. 7, an electrosurgical instrument according to another embodiment of the present disclosure may include a lever 710 having a flange or ram 712 configured to activate the electrosurgical instrument 20. When lever 710 is depressed, ram 712 stresses and/or flexes fuse 722 to weaken fuse 722. Fuse 722 may be designed to break after flange 712 rams fuse 722 a predetermined number of times.

Although the above described embodiments disclose a recess in the prong of a plug and a protrusion in the receptacle of the electrosurgical generator, in alternative embodiments, the receptacle may include a recess, while the prong includes the protrusion.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. The claims can encompass embodiments in hardware, software, or a combination thereof. Those skilled in the art will envision other modifications within the scope and spirit of the claims appended hereto.

What is claimed is:

1. An electrosurgical system comprising:
    an electrosurgical generator configured to output electrosurgical energy, the electrosurgical generator including a receptacle having at least one mechanical interface;
    an electrosurgical instrument adapted to connect to the electrosurgical generator and configured to deliver energy to tissue; and
    a plug configured to engage the receptacle to electrically couple the electrosurgical instrument to the electrosurgical generator, the plug including;
        a terminal electrically coupled to the electrosurgical instrument; and
        a prong electrically coupled to the terminal, the prong including a recess defined therein and configured to receive the at least one mechanical interface,
    wherein when the plug is disengaged from the receptacle, the at least one mechanical interface cooperates with the recess to uncouple the prong from the terminal.

2. The electrosurgical system according to claim 1, wherein the prong includes a pair of contacts that are electrically coupled to the terminal.

3. The electrosurgical system according to claim 2, wherein the prongs are biased in a spaced apart configuration.

4. The electrosurgical system according to claim 3, wherein the plug includes at least one tab and wherein upon disengagement of the plug from the receptacle the pair of contacts move proximally relative to the at least one tab thereby breaking the electrical coupling between the terminal and the prong.

5. The electrosurgical system according to claim 1, wherein the plug includes a chamber defined therein filled with a conductive medium that provides electrical continuity between the terminal and the prong and wherein and a distal end of the prong seals the chamber.

6. The electrosurgical system according to claim 5, wherein upon disengagement of the plug from the receptacle, the conductive medium is released from the chamber thereby eliminating electrical continuity between the terminal and the prong and preventing further use of the electrosurgical instrument.

7. The electrosurgical system according to claim 5, wherein the conductive medium is argon.

8. An electrosurgical system comprising:
    an electrosurgical generator configured to output electrosurgical energy, the electrosurgical generator including a receptacle having at least one mechanical interface; and
    an electrosurgical instrument adapted to connect to the electrosurgical generator and configured to deliver energy to tissue; and
    a plug configured to engage the receptacle to electrically couple the electrosurgical instrument to the electrosurgical generator, the plug including;
        a conduit electrically coupled to the electrosurgical instrument;
        a prong configured to be electrically coupled to the receptacle; and
        a fuse electrically coupling the conduit to the prong,
    wherein when the plug is disengaged from the receptacle, the at least one mechanical interface breaks the fuse to uncouple the prong from the conduit.

9. The electrosurgical system according to claim 8, wherein the fuse is a wire.

10. The electrosurgical system according to claim 8, wherein the mechanical interface is a fuse cutter configured to cut the fuse.

11. The electrosurgical system according to claim 8, wherein the mechanical interface is a ram configured to stress and/or flex the fuse to break the fuse.

* * * * *